United States Patent
Shinno et al.

(10) Patent No.: US 7,869,859 B2
(45) Date of Patent: Jan. 11, 2011

(54) X-RAY CT APPARATUS HAVING A DISPLAY TO DISPLAY INFORMATION INPUTTED FROM A REMOTE OPERATOR CONSOLE

(75) Inventors: Toshiyuki Shinno, Tochigi-ken (JP); Hiroyuki Ooishi, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1358 days.

(21) Appl. No.: 10/383,594

(22) Filed: Mar. 10, 2003

(65) Prior Publication Data
US 2004/0181142 A1  Sep. 16, 2004

(51) Int. Cl.
A61B 5/05 (2006.01)
(52) U.S. Cl. .................................. 600/425; 378/98
(58) Field of Classification Search ............... 600/418, 600/407, 425; 250/370.09; 378/98–98.12, 378/4, 21
See application file for complete search history.

(56) References Cited

U.S. PATENT DOCUMENTS

| | | | | |
|---|---|---|---|---|
| 4,296,756 A | * | 10/1981 | Dunning et al. | 600/529 |
| 4,696,030 A | * | 9/1987 | Egozi | 379/167.01 |
| 5,017,870 A | * | 5/1991 | Kasugai et al. | 324/318 |
| 5,025,374 A | * | 6/1991 | Roizen et al. | 600/300 |
| 5,339,813 A | * | 8/1994 | DeYoe et al. | 600/418 |
| 5,355,885 A | * | 10/1994 | Tsuda et al. | 600/418 |
| 5,412,419 A | * | 5/1995 | Ziarati | 348/61 |
| 5,464,014 A | * | 11/1995 | Sugahara | 600/411 |
| 5,533,082 A | * | 7/1996 | Gronemeyer et al. | 378/20 |
| 5,546,943 A | * | 8/1996 | Gould | 600/425 |
| 5,861,865 A | * | 1/1999 | Anand et al. | 345/658 |
| 5,877,732 A | * | 3/1999 | Ziarati | 345/8 |
| 5,978,697 A | * | 11/1999 | Maytal et al. | 600/411 |
| 6,035,228 A | * | 3/2000 | Yanof et al. | 600/429 |
| 6,063,030 A | * | 5/2000 | Vara et al. | 600/437 |
| 6,872,179 B2 | * | 3/2005 | Kamiyama et al. | 600/437 |
| 7,182,083 B2 | * | 2/2007 | Yanof et al. | 128/204.23 |

FOREIGN PATENT DOCUMENTS

JP  5-269117  10/1993
JP  2000-311194  11/2000

* cited by examiner

Primary Examiner—Brian Casler
Assistant Examiner—Parikha S Mehta
(74) Attorney, Agent, or Firm—Oblon, Spivak, McClelland, Maier & Neustadt, L.L.P.

(57) ABSTRACT

A medical apparatus including a main unit including an X-ray CT imaging unit configured to image a patient and a display unit provided on the X-ray CT imaging unit and configured to display a name of the patient to be imaged, and a console unit remote from the main unit and including an input unit configured to input condition information of the main unit and individual information including the name of the patient. The console also includes a control unit configured to extract at least one item including the name of the patient in the individual information from the inputted condition information and the inputted individual information. The display unit is configured to display the extracted item including the name of the patient on a screen.

16 Claims, 7 Drawing Sheets

FIG. 5A  Ms. NIHON HANAKO

FIG. 5B  20 SECONDS REMAINS

FIG. 5C  ★★★☆☆

FIG. 5D  STOP BREATH

FIG. 5E  RELEASE BREATH

X-RAY CT APPARATUS HAVING A DISPLAY TO DISPLAY INFORMATION INPUTTED FROM A REMOTE OPERATOR CONSOLE

CROSS-REFERENCE TO RELATED APPLICATIONS

This application incorporates the entire content of Japanese Patent Application No. P2001-246873, filed Aug. 16, 2001.

FIELD OF THE INVENTION

The present invention relates to a medical apparatus, such as a treatment apparatus for treating a patient or a medical imaging apparatus for imaging a patient.

BACKGROUND OF THE INVENTION

Conventionally various types of medical apparatus, such as an X-ray diagnostic apparatus, an X-ray computed-tomography (X-ray CT) apparatus, a magnetic resonance imaging (MRI) apparatus, a nuclear medicine apparatus, a radiotherapy treatment apparatus, a shock wave treatment apparatus, or a warm temperature treatment apparatus are used for contributing to medical improvements of illness diagnosis, progress observation or medical treatment. For instance, an X-ray diagnostic apparatus, an X-ray CT apparatus, an MRI apparatus, and a nuclear medicine apparatus are used for obtaining a medical image of a patient for diagnosis. A radiotherapy apparatus, a shock wave treatment apparatus, and a warm temperature treatment apparatus are used for treating a part of a patient.

A hospital where these apparatuses are installed is systematized for saving medical staff's labors. The medical staff is specialized. Usually, each of these medical apparatuses is placed in a specific examination room or a treatment room (hereinafter both rooms are simply referred as an "inspection room"). To be imaged or treated, a patient is carried into the inspection room on a stretcher. In such a situation, after a medical staff checks a patient name, a doctor obtains a medical image of the patient or treats the patient. Before imaging or treating, individual information of a patient, such as a patient ID, name, sex, or a birth date, and condition information for imaging or treating (hereinafter called "inspection condition information"), are inputted into a medical apparatus.

A conventional medical diagnostic imaging apparatus, as disclosed in Japanese Patent Publication No. 5-269117, has two input devices. Each input devices has the same function. One of the input devices is placed in a room where an operator operates the medical diagnostic imaging apparatus, and the other is installed on a gantry of the medical diagnostic imaging apparatus. A system including these two input devices is called as a double console system. By these input devices, a staff can input and refer to a patient's individual information and inspection condition information.

In addition, there is an identification (ID) system, as disclosed in Japanese Patent Publication (Kokai) No. 2000-311194, for identifying a particular patient. To identify the patient by this ID system, the patient has a non-contacting data career for storing an individual data. A portable reading device reads the individual data. According to the ID system, misidentification of a patient, especially an inpatient, may be decreased.

However, when a patient name is checked by the double console system, it is difficult for a busy medical staff to find a particular patient name among a multiplicity of information, e.g., patient's individual information, such as a patient ID, a name, sex, birth date, and inspection condition information, and so on. For example, in operating an X-ray CT apparatus, the patient name has to be found out from a plurality of inspection condition information, such as insertion direction information (whether a patient is inserted from a leg or a head to a gantry), field of view (FOV) information, X-ray tube current information and imaging part, e.g., head or leg information (in addition to the patient's individual information). Also operating in an MRI apparatus, the patient name has to be found out from a plurality of inspection condition information, such as insertion direction information, field of view (FOV) information, pulse sequence information, e.g., repetition time and imaging part, e.g., head or leg information in addition to the patient's individual information of the patient. Initially, an operator inputs the patient's individual information and the inspection condition information by a console provided in a room outside an inspection room. Next, using the other console placed at a gantry, a medical staff in the inspection room where the apparatus is placed, searches information of a patient who will be imaged or treated. Further the medical staff has to pick up the patient's individual information related to the searched patient. Accordingly, since each console in the conventional double console system has the same function, it is very hard to check the patient's individual information, such as the patient name.

The identification system is complex to operate, and additionally it requires great initial investment and is expensive to operate.

SUMMARY OF THE INVENTION

The present invention intends to solve the above-mentioned problems. Accordingly, the present invention provides a medical apparatus that may easily decrease misidentification of a particular patient. Consistent with the present invention, there is provided a medical apparatus comprising a main unit configured to treat or image an object, an input unit configured to input condition information of the main unit and individual information of the object, a control unit configured to extract at least one item in the individual information from the inputted condition information and the inputted individual information, and a display unit configured to display the extracted item on a screen. Also consistent with the present invention, there is provided a medical apparatus comprising a main unit configured to treat or image an object, a display unit configured to display a name of the object on a screen, an input unit configured to input confirmation information when the object confirms the displayed name, and a notification unit configured to notify an operator operating the main unit that the confirmation information is inputted. Also consistent with the present invention, there is provided a method, for controlling a medical apparatus, comprising inputting condition information of a main unit configured to treat or image an object and individual information of the object, extracting at least one item in the individual information from the inputted condition information and the inputted individual information, and displaying the extracted item on a screen.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. Wherever possible, the same reference numbers will be used throughout the drawings to the same or the like parts. In the drawings.

DETAILED DESCRIPTION OF THE INVENTION

Figure 1:
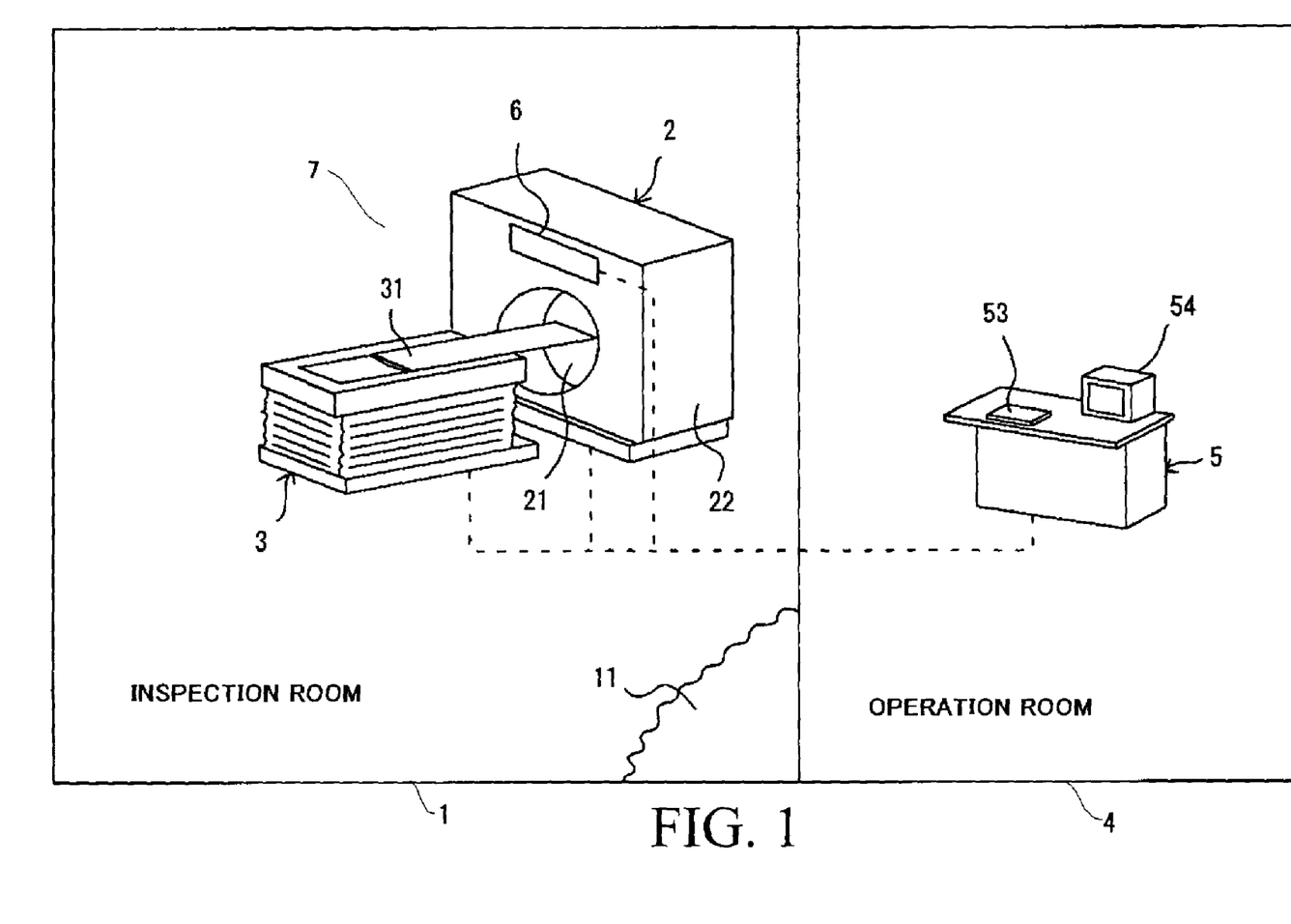
FIG. 1 is a perspective view of a medical apparatus according to an embodiment consistent with the present invention.

Reference will now be made in detail to the exemplary embodiments of the invention, examples of which are illustrated with reference to FIG. 1 to FIG. 6. As illustrated in FIG. 1, an inspection room 1 in a hospital, a gantry 2 of an X-ray CT apparatus and a patient carrying bed 3 (hereinafter collectively called as a main part 7) are provided. Further, in an operation room 4 next to the inspection room 1, a console 5 is provided for controlling the main part 7. A display unit 6 is provided on a surface of the gantry 2 of the X-ray CT apparatus. Dotted lines are signal lines for electrically connecting between the console 5 and the main part 7 including the display unit 6. The display unit 6 displays a patient name being inspected by the main part 7 of the X-ray CT apparatus. A color liquid crystal display (LCD) unit or a light emitting diode (LED) unit is suitable for the display unit 6. Of course, other types of various display units may be used. The LCD unit and the LED unit may display a patient name not only in some character forms, such as a Chinese character form, a Japanese KATANAKA form, a Roman alphabet form, and an English form but also in some color forms. For instance, it may be possible to display a different color for a man or a woman. By using these forms, a patient can be easily identified.

Figure 2:
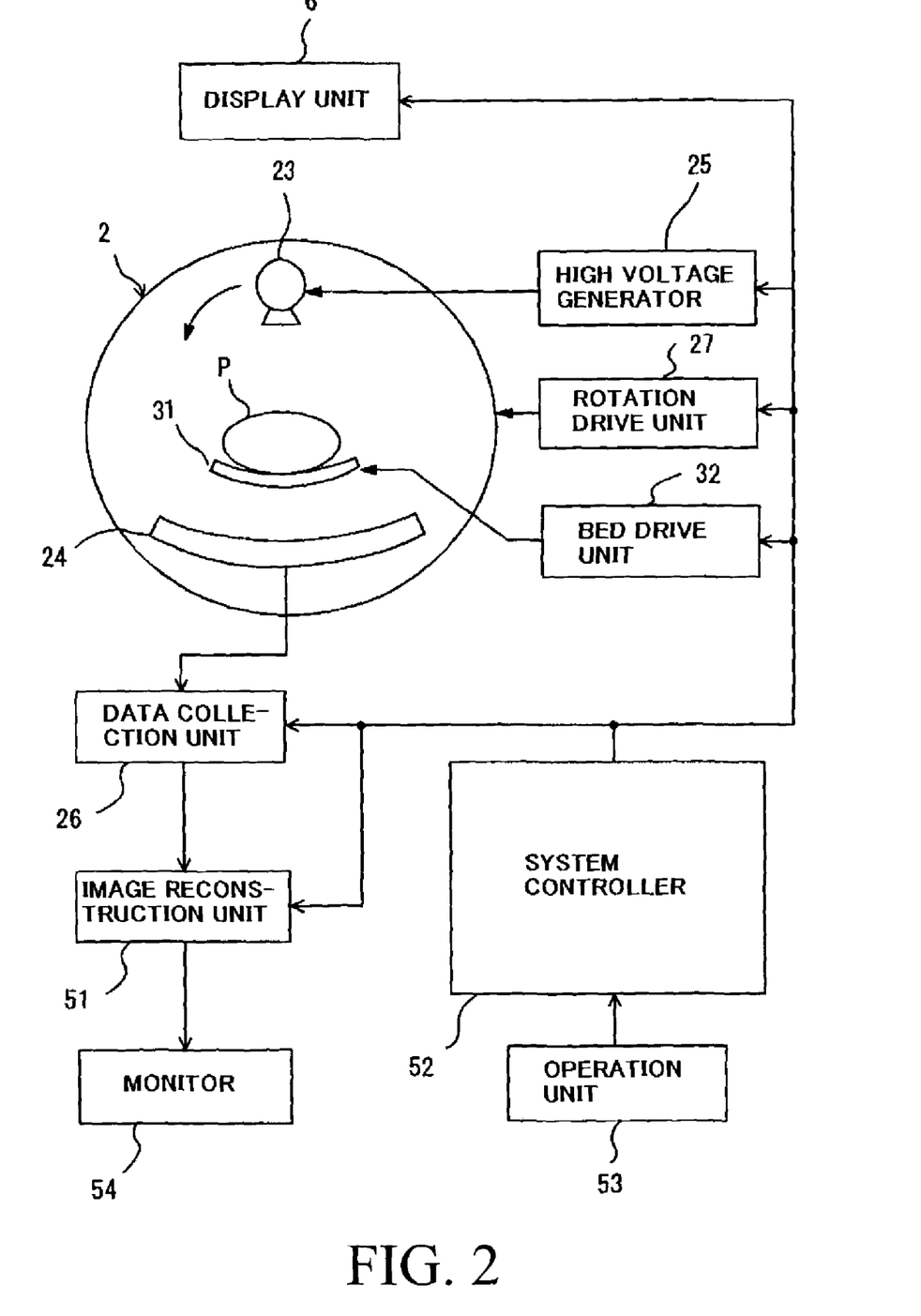
FIG. 2 is a block diagram of an X-ray CT apparatus applied in the first embodiment.

FIGS. 1 and 2 illustrate the details of the X-ray CT apparatus. As shown in FIG. 1, gantry 2 has a central aperture 21 for inserting a patient P laid on a bed plate 31. Usually, an inside of the gantry 2 cannot be seen, since a surface of the gantry 2 is covered with a cover unit 22. The gantry 2 includes an X-ray tube 23 and an X-ray detector 24 that are arranged so as to place a patient between them. A high voltage generator 25 supplies an X-ray tube current and a voltage to the X-ray tube 23, a data collection unit 26 collects projection data of the patient P obtained by the X-ray detector 24, and a rotation drive unit 27 rotates the X-ray tube 23 and the X-ray detector 24 around the patient P. As shown in FIG. 1, bed plate 31 is driven in a longitudinal direction to place the patient P at an appropriate position in the aperture 21 for imaging. The console 5 includes an image reconstruction unit 51 for reconstructing an image based on the projection data collected by the data collection unit 26 and a system controller 52 that includes a computer and a memory, for controlling the data collection unit 26, the image reconstruction unit 51, the high voltage generator 25, the rotation drive unit 27, the bed drive unit 32, e.g.. As shown in FIG. 1, the console 5 includes an operation unit 53 for inputting various setting values and commands by an operator. Further, the console 5 includes a monitor 54 for displaying inputted information and a reconstructed image.

Figure 3:
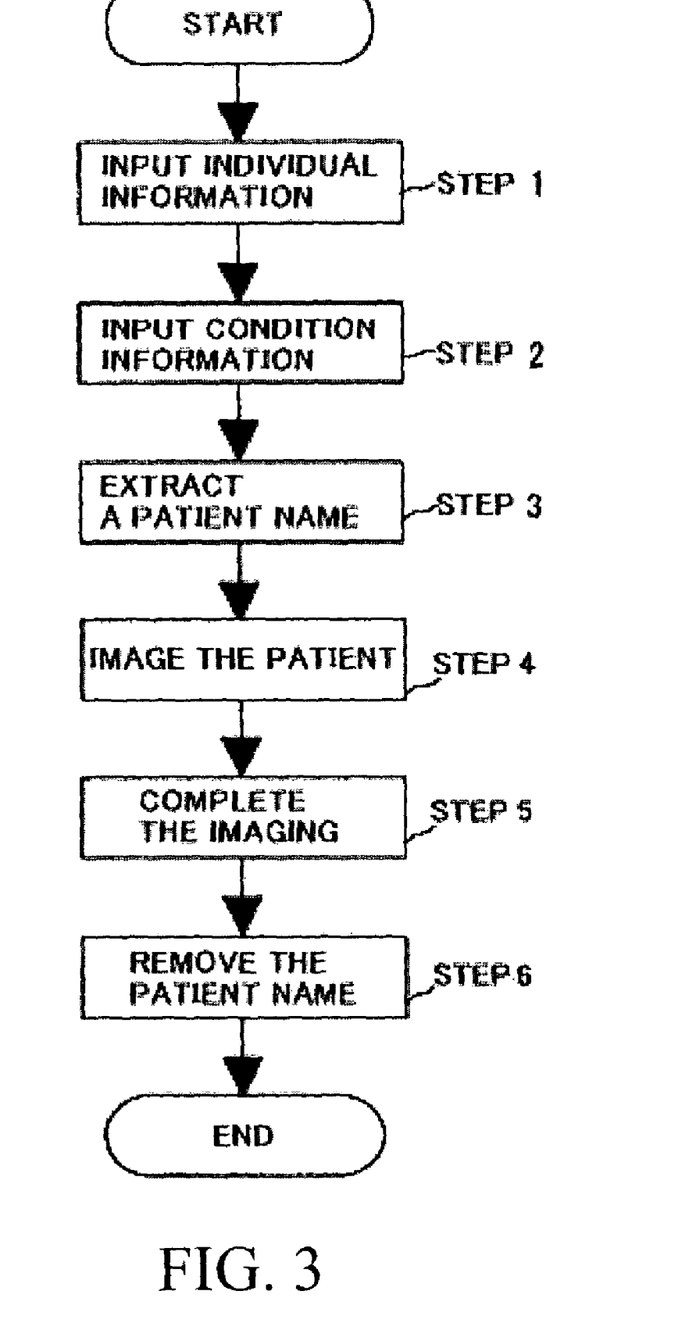
FIG. 3 is a flow chart for explaining an operation of the X-ray CT apparatus.

FIG. 3 shows a procedure for collecting a medical image of a patient P. Before imaging, by using the operation unit 53 shown in FIG. 1, an operator inputs patient's individual information, such as patient ID, name, sex, and birth date, while seeing the inputted information displayed on a of a monitor 54 shown in FIG. 1. The inputted patient's individual information is stored in a memory of a system controller 52 (Step 1). If a plurality of patients is successively imaged, each patient's individual information may be inputted in advance. Next, an operator inputs an inspection plan including inspection condition information in accordance with a particular patient P (Step 2). After confirming the inputted inspection plan, the operator inputs determination information by the operation unit 53 to determine the patient's individual information and the inspection plan. Accessing the patient's individual information in accordance with the determination operation, the system controller 52 extracts only the patient name to display the extracted patient name on the display unit 6 provided on a surface of the gantry 2 of the X-ray CT apparatus (Step 3). In this embodiment, the patient name only is extracted. Of course, it is possible to extract, other patient's individual information, such as sex or birth date.

When a medical staff calls a name of the patient P in a waiting room, the patient P comes into an inspection room 1. At this time, the patient P can look at his name on the display unit 6. Thus, it becomes possible for the patient who is going to be inspected to confirm his name in the inspection room. The patient P changes to inspection clothes in a changing corner 11, shown in FIG. 1, in the inspection room 1. The changing corner 11 is separated from an inspection place by, for example, a curtain. After changing clothes, the patient P lies on the bed plate 31 in accordance with an instruction of a medical staff. An operator enters the inspection room 1 to explain about the imaging to the patient P. The operator or a medical staff adjusts a position of the patient P. The operator and the medical staff move to the operation room 4 to image the patient P according to an inspection plan (Step 4). If there is a problem, the imaging is continued with confirming the images by the operator. If there is no problem, the operator inputs the end information with the operation unit 53 to complete the imaging (Step 5). According to this end operation, the system controller 52 initializes the inspection plan and the display unit 6 removes the patient name from a screen (Step 6). After the medical staff informs the patient P of the completion of the inspection, the patient P wears his own clothes to leave the inspection room 1. The operator or another special doctor diagnoses the patient P based on the patient's medical image copied to a film or displayed on a monitor to make a report for describing a result of the diagnosis. At this time, the patient's individual information, such as the patient name and the patient ID, is also copied to the film or displayed on the monitor according to control of the system controller 52. The same patient's individual information also is included in the report.

Since the patient name is extracted from the inputted patient's individual information by the system controller 52 to be displayed on the display unit 6, as one of the routine operations, the patient P coming into the inspection room 1 can confirm his name by himself, which avoids misidentification of the patient. If the displayed name on the display unit 6 is incorrect, the patient may inform the error to the medical staff. Consequently, the misidentification can be quickly corrected. If the patient is carried to the inspection room 1 by a stretcher, the medical staff or an attendant person can check the displayed name to correct the misidentification in advance. Moreover, since the patient's individual information, such as the patient name and the patient ID, is copied to a film or displayed on a monitor with the image or included in the report where the diagnosis result is described, the result can be associated with the patient even after inspection.

In this embodiment, the display unit 6 where the patient name is displayed is placed on the surface of the gantry 2 of the X-ray CT apparatus. Of course, the present invention is not limited to the specific details and can be modified as other embodiments explained below.

Figure 4:
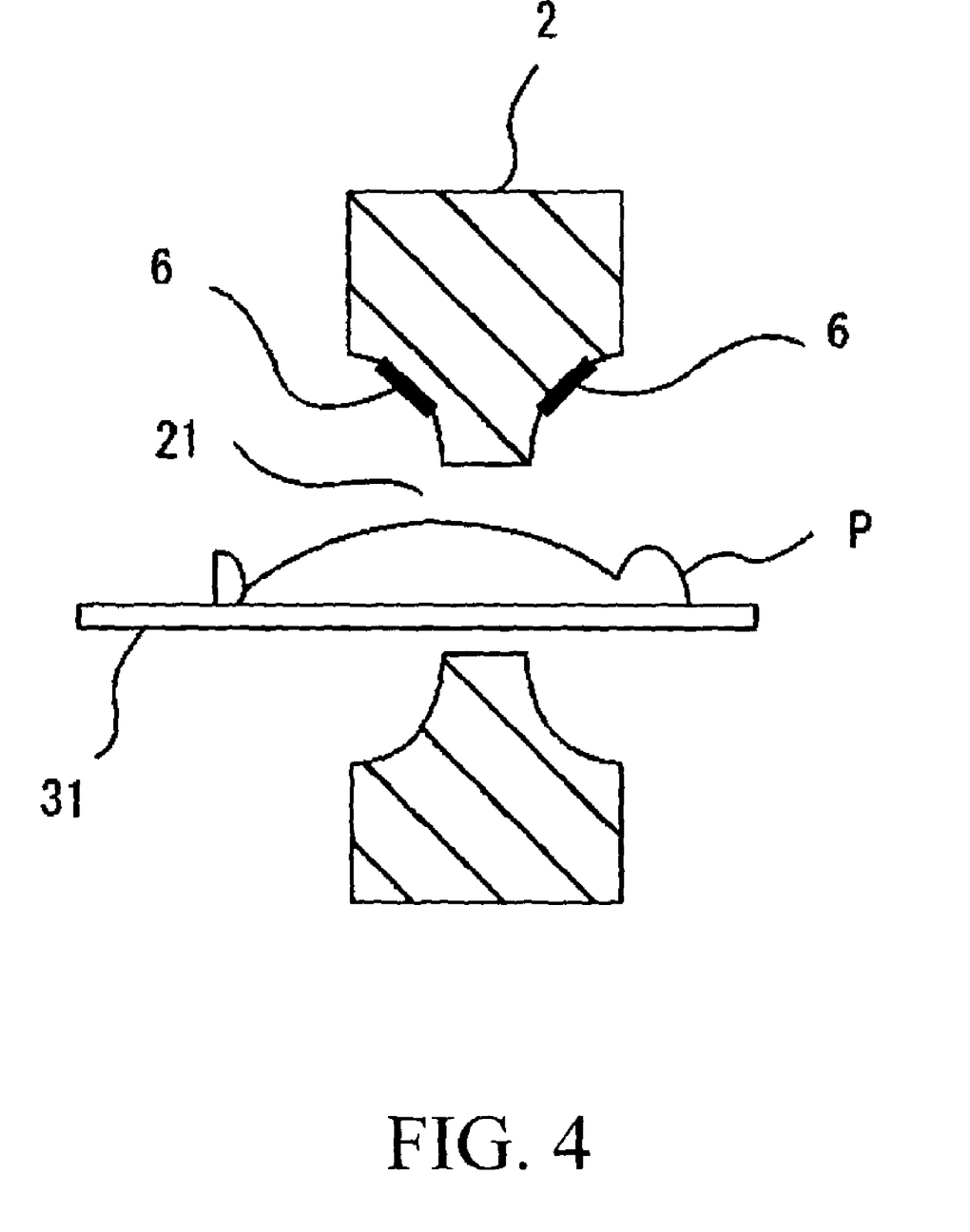
FIG. 4 is a sectional view of a modified embodiment of a gantry in an X-ray CT apparatus.

FIG. 4 is a cross-sectional view of a gantry of an X-ray CT apparatus according to another embodiment. A peripheral portion around an aperture 21 of a gantry 2 includes a gradually sloped part for placing a display unit 6. Thus, when a patient P laid on the bed plate 31 is inserted in the aperture 21 of the gantry, the display unit 6 comes into a patient's view. The display unit 6 may be placed at an inside part of the aperture 21 instead of the sloping part. In this embodiment, a respective display unit 6 is placed at each side of the gantry. Of course, it is possible to place the display unit at one side only.

Figure 5A:
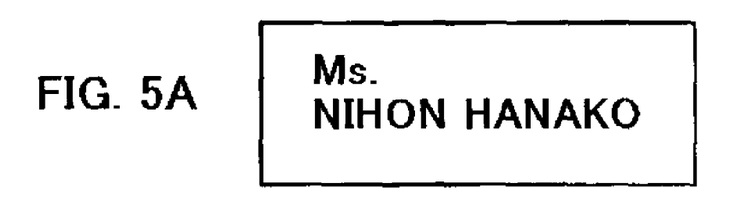
FIGS. 5A-5E illustrate examples of a displayed screen.

According to this embodiment, various types of information can be displayed on the display unit 6 as shown in FIGS. 5A-5E. As shown in FIG. 5A, a patient name is kept displaying until inspection is started. When the inspection is started, situation information of the inspection, such as time information of an end of the inspection, or instruction information to the patient, such as breath information, may be displayed as a character, or a mark. As another example, the instruction information may include waiting information to keep the patient waiting between a pre-imaging and a main imaging. The pre-imaging may be a scanogram imaging, and the waiting information instructs the patient to keep waiting while an operator sets FOV on the scanogram.

Figure 5B:
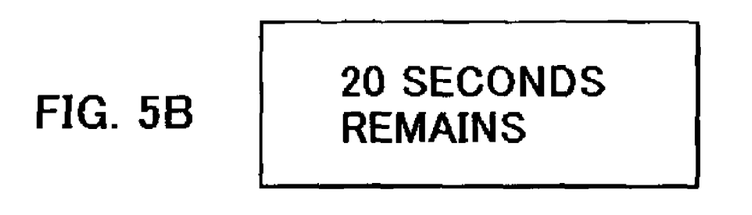
Figure 5C:
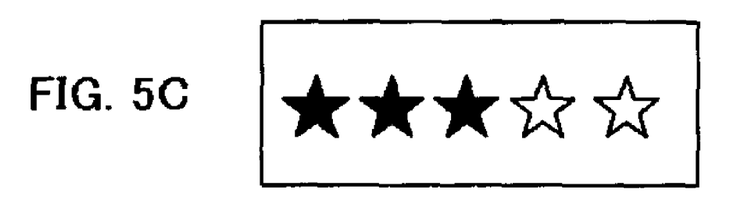
Figure 5D:
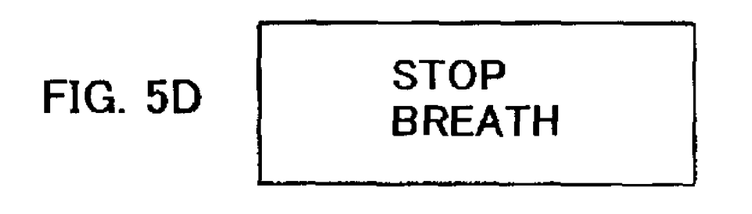
Figure 5E:
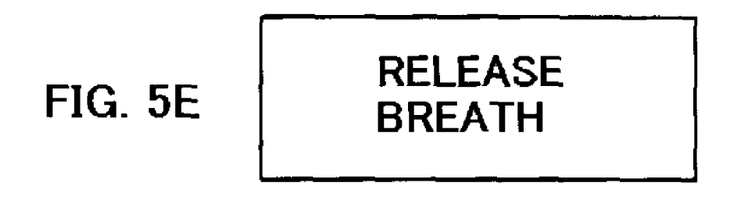

FIG. 5B shows the time information indicating residual time to the end of the inspection as a numerical indication and FIG. 5C shows it as a star indication having a plurality of star marks that are turned on in an order according to a predetermined time. FIGS. 5D and 5E show the breath information that respectively instructs the patient to stop and release a breath. These types of information make it possible not only to confirm a patient name but also to quiet the patient's fear for the inspection. The display unit 6 may be placed at a part where the patient can easily find it, such as near a bed.

Figure 6:
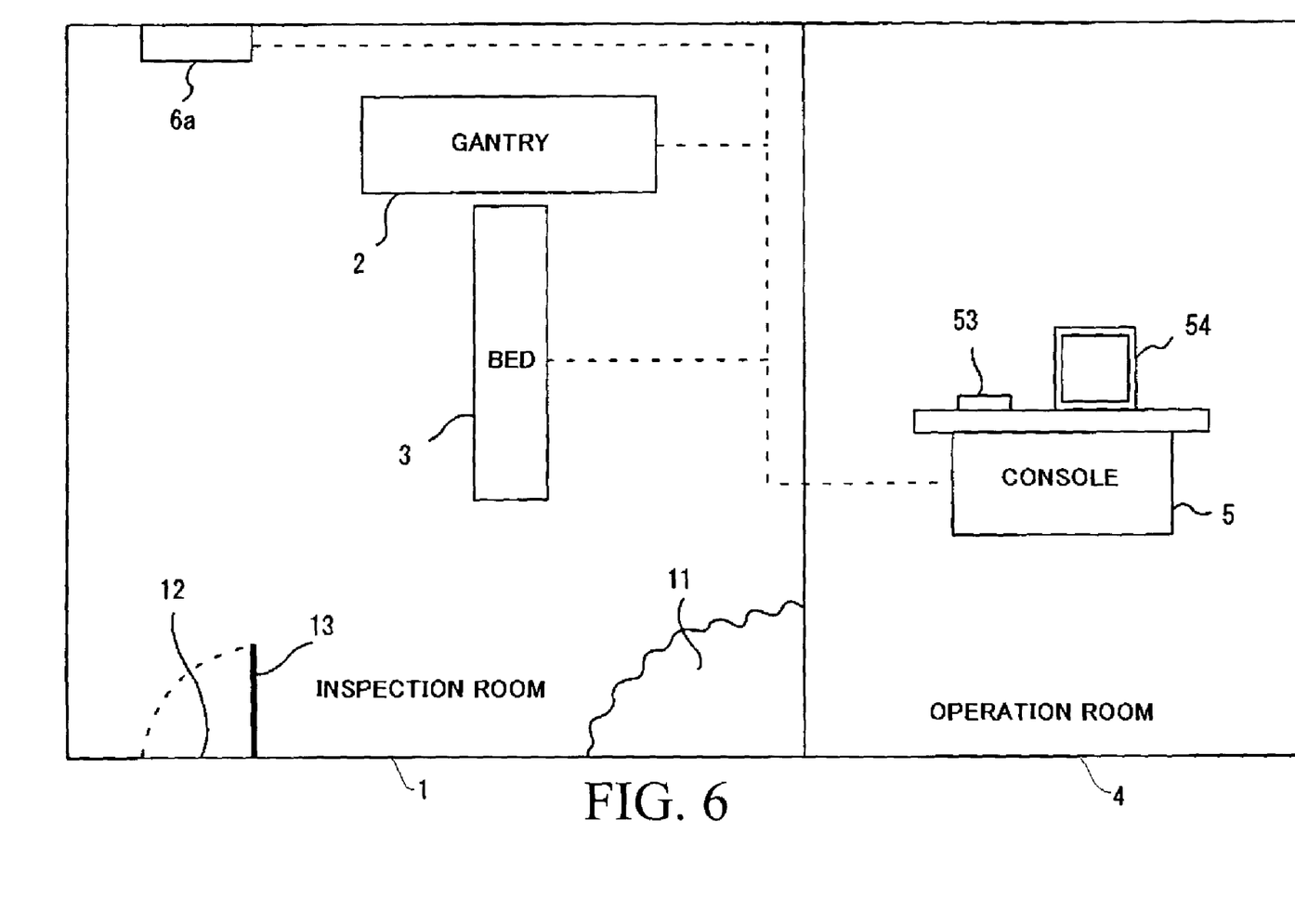
FIG. 6 is a schematic perspective view of an X-ray CT apparatus according to another embodiment consistent with the invention.

FIG. 6 illustrates another embodiment. A display unit 6A similar to the display unit 6 is located on a surface of a wall of an inspection room 1 and faces an entrance 12 of the inspection room 1. The display unit 6A displays a patient name confirmed by an operator. Thus, when the entrance door 13 of the inspection room 1 is opened, the patient P can confirm his name on the display unit 6A. To simplify the explanation, the other explanations of the construction of this embodiment are omitted by attaching the same reference numbers in FIG. 6 as illustrated in FIG. 1. The display unit 6A may be similarly located on a place which is easy for a patient to see in the inspection room 1. Of course, the display unit 6A may not be located on the inside surface of the wall of the inspection room 1, but may be located on an outside surface of the wall near the entrance 12 of the inspection room 1 instead.

Figure 7:
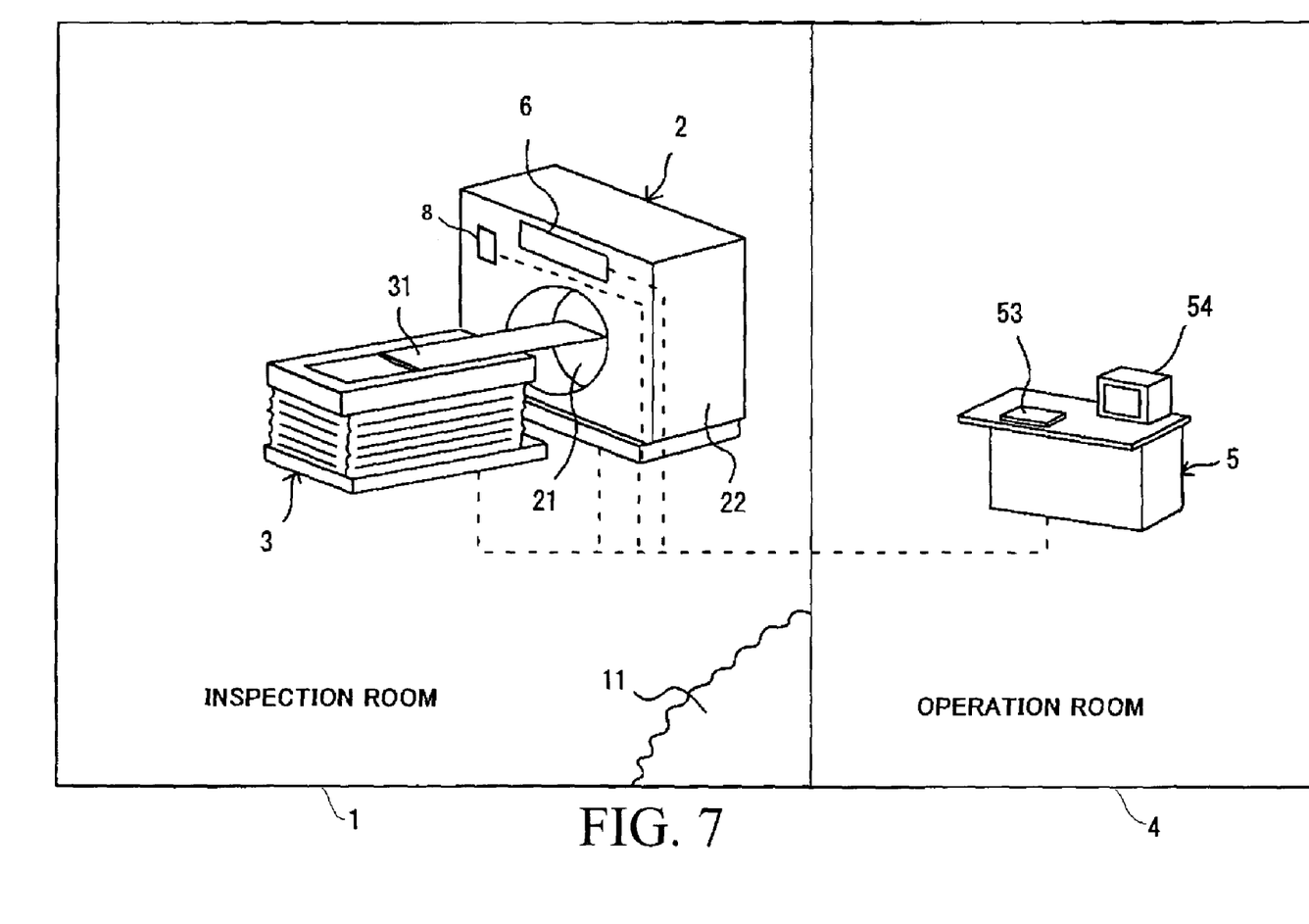
FIG. 7 is a perspective view of an X-ray CT apparatus according to another embodiment.

FIG. 7 explains a further embodiment of the invention which includes an input device 8 to input confirmation information. This input device 8 is provided on a gantry 2 near a display unit 6. When the patient confirms his name displayed on the display unit 6, he pushes a button of the input device 8 in order to confirm the displayed information. The confirmed information is transmitted to a console 5 to be displayed on a monitor 54 in an operation room 4. Accordingly, an operator operating the console 5 can recognize that the patient has confirmed that the displayed name corresponds to his name. While, if the displayed name does not correspond to the patient's name, the patient does not push the above-mentioned button. The console 5 controls a main part 2 to postpone imaging the patient until the patient name is correctly confirmed. i.e., until the button is pushed. An attendant or an operator or a medical staff who can confirm that a displayed name corresponds to the patient' name by asking the patient may push the button. The input device 8 may includes another button for postponing imaging the patient. Still further, another embodiment of the invention may include a lamp provided at a position where an operator can observe, such as near a gantry 22. The lamp turns ON when the patient name is confirmed. Moreover, it is also possible to remove the patient's name from the display screen 6 if the button of the input device 8 is pushed.

The present invention is not limited to a medical apparatus fixed in a facility, such as a hospital, but is also applicable to a mobile medical apparatus installed in a medical vehicle that services areas of low population. Also the present invention is not limited to an X-ray CT apparatus but is applicable to various medical apparatuses including a treatment apparatus and a medical imaging apparatus. For example, the medical imaging apparatus may be an X-ray diagnostic apparatus, a MRI apparatus, and a nuclear medicine apparatus, and the treatment apparatus may be a radiotherapy apparatus, such as a linear accelerator apparatus, a microtron apparatus, a betatron apparatus, and an apparatus using a cobalt 60. Further the treatment apparatus may be an impulse therapy apparatus, such as an impulse wave medical treatment apparatus and a warm temperature medical treatment apparatus using microwave or ultrasound. As another example, if there is a clothing changing room near an inspection room, the display unit 6A may possible to locate in the clothing changing room.

Further, if there is a waiting room for an inspection, a display unit 6A may be located in the waiting room. In this case, it is not necessary to keep displaying a patient's name on the display unit 6A after the patient enters the inspection room from the waiting room. Accordingly, the display unit 6A may remove the patient name from a screen when the patient is confirmed to enter the inspection room.

Further, a voice generator for generating voice information by transforming electrical information of a patient name to the voice information to output the voice information as sound, such as "Mr. __________. Please enter an inspection room." may be provided.

As another example, there may be a plurality of display units displaying simultaneously the same patient name, which is more effective for preventing misidentification of the patient.

The present invention is not limited to the above embodiments, and various modifications may be made without departing from the spirit or scope of the general inventive concept.

What is claimed is:

1. A medical system, comprising:
   a main unit including a gantry in which an X-ray tube and an X-ray detector are provided;
   a display unit provided on the gantry and configured to display a name of a patient to be imaged;
   an input device provided on the gantry adjacent to the display unit and configured to receive input from the patient that confirms whether the name displayed on the display unit is accurate or not, and configured to transmit confirmation information indicating that the name displayed on the display unit is accurate when receiving the input from the patient; and a console unit remote from the main unit and including a processor configured to control imaging by the main unit and configured to postpone the imaging by the main unit until the console unit receives the confirmation information transmitted, in response to the input from the patient, from the input device provided on the gantry indicating that the name displayed on the display unit is accurate.

2. The medical system according to claim 1, wherein the console unit is configured to extract a name of the patient from the individual information received by the input device.

3. The medical system according to claim 1, wherein the input unit is provided in a different room from a room where the main unit is provided.

4. The medical system according to claim 1, wherein the display unit is provided on the gantry in such a position that the patient to be imaged can see the display unit.

5. The medical system according to claim 1, wherein the display unit is arranged in a position on or near a peripheral portion around an aperture of the main unit.

6. The medical system according to claim 1, wherein the display unit is arranged in a same room as the main unit.

7. The medical apparatus according to claim 1, wherein the display unit includes a color LCD unit or an LED unit.

8. The medical apparatus according to claim 1, wherein the input unit receives determination information to determine received condition information and received individual information; and the display unit starts to display an item extracted from the received individual information or the received condition information when the determination information is received.

9. The medical apparatus according to claim 1, further comprising a voice generation unit configured to generate voice information of an item extracted from information received by the input device.

10. The medical apparatus according to claim 1, wherein the display unit ceases to display an item extracted from information received by the input device when treating or imaging of the patient is completed.

11. The medical apparatus according to claim 1, wherein the display unit displays situation information of treating or imaging of the patient when the treating or the imaging of the patient starts.

12. The medical apparatus according to claim 1, further comprising a memory unit configured to store an item extracted from information received by the input device in addition to an image of the patient.

13. The medical apparatus according to claim 1, wherein the display unit displays waiting information to keep the patient waiting between a pre-imaging and a main imaging.

14. A method for controlling a medical apparatus, comprising:

displaying a name of a patient to be imaged on a display unit provided on a gantry of a main unit in which an X-ray tube and an X-ray detector are provided;

receiving, from an input device provided on the gantry adjacent to the display unit, input information from the patient that confirms whether the name displayed on the display unit is accurate or not;

transmitting, from the input device to a console unit remote from the main unit confirmation information indicating that the name displayed on the display unit is accurate, when receiving the input information from the patient; and controlling, by the console unit remote from the main unit, imaging by the main unit, and postponing the imaging when the confirmation information transmitted from the input device indicates that the name displayed on the display unit is not accurate.

15. The medical system of claim 1, wherein the input device provided on the gantry includes a button, and the input device is configured to transmit the confirmation information to the console when the patient pushes the button to confirm that the name displayed on the display unit is accurate.

16. The medical system of claim 15, further comprising a controller configured to cause the display unit to remove the name of the patient displayed on the display unit when the button of the input device is pushed by the patient.

* * * * *